United States Patent [19]
Reading

[11] Patent Number: 5,624,187
[45] Date of Patent: Apr. 29, 1997

[54] METHOD AND APPARATUS FOR GAS FLOW MODULATED DIFFERENTIAL SCANNING CALORIMETRY

[75] Inventor: Michael Reading, London, England

[73] Assignee: TA Instruments, Inc., New Castle, Del.

[21] Appl. No.: 459,022

[22] Filed: Jun. 2, 1995

Related U.S. Application Data

[63] Continuation-in-part of Ser. No. 171,656, Dec. 22, 1993, Pat. No. 5,439,291, which is a continuation-in-part of Ser. No. 60,214, May 7, 1993, Pat. No. 5,346,306, which is a continuation of Ser. No. 844,448, Mar. 2, 1992, Pat. No. 5,224,775.

[51] Int. Cl.$^6$ .................................................. G01N 25/00
[52] U.S. Cl. .............................................. 374/11; 374/31
[58] Field of Search ............................... 374/10, 11, 12, 374/13, 31, 33, 36, 43, 110, 124, 166, 39, 40, 41; 165/104.19, 104.32, 104.34

[56] References Cited

U.S. PATENT DOCUMENTS

| | | |
|---|---|---|
| 2,975,629 | 3/1961 | Herbert . |
| 3,263,484 | 8/1966 | Watson et al. . |
| 3,271,996 | 9/1966 | Paulik et al. . |
| 3,339,398 | 9/1967 | Barrall, II et al. . |
| 3,360,993 | 1/1968 | MacMillan . |
| 3,417,604 | 12/1968 | Bean et al. . |
| 3,527,081 | 9/1970 | Hill . |
| 3,732,722 | 5/1973 | Norem et al. . |
| 3,789,662 | 2/1974 | Zettler et al. . |
| 4,095,453 | 6/1978 | Woo . |
| 4,255,961 | 3/1981 | Biltonen et al. . |
| 4,350,446 | 9/1982 | Johnson . |
| 4,690,569 | 9/1987 | Veitch . |
| 4,783,174 | 11/1988 | Gmelin et al. . |
| 4,787,698 | 11/1988 | Wickramasinghe et al. . |
| 4,812,051 | 3/1989 | Paulik et al. . |
| 4,838,706 | 6/1989 | Coey et al. . |
| 4,840,496 | 6/1989 | Elleman et al. . |

(List continued on next page.)

FOREIGN PATENT DOCUMENTS

| | | |
|---|---|---|
| 0051266 | 5/1982 | European Pat. Off. . |
| 0380414 | 8/1990 | European Pat. Off. . |

OTHER PUBLICATIONS

N. Birge and S. Nagel, "Specific-Heat Spectroscopy of the Glass Transition," Physical Review Letters, vol. 54, No. 25, Jun. 24, 1985, pp. 2674–2677.

N. Birge, "Specific-heat spectroscopy of glycerol and propylene glycol near the glass transition", Physical Review B, vol. 34, No. 3, Aug. 1, 1986, pp. 1631–1642.

(List continued on next page.)

*Primary Examiner*—G. Bradley Bennett
*Attorney, Agent, or Firm*—Crowell & Moring LLP

[57] ABSTRACT

A modulated differential scanning calorimeter ("MDSC") wherein the temperature of the sample and/or the reference is modulated by modulating the characteristics of a gas in thermal contact with the sample and or a reference. In a first embodiment, the major heat flow path between the sample/reference and the furnace is the purge gas in the furnace chamber. The composition of the purge gas in the furnace chamber of the DSC cell is modulated by alternately purging the DSC cell with a high thermal conductivity gas (e.g., helium) and with a low thermal conductivity gas (e.g., nitrogen), thus modulating the flow of heat to and from the cell. In a second embodiment, the sample and reference are heated (or cooled) by a temperature-controlling gas flowing around the sample and reference holders. The gas is heated by being passed through a furnace before it flows around the sample and the reference. The flow-rate of the temperature-controlling gas is modulated, thus modulating the temperature of the sample and the reference. The third embodiment is similar to the second embodiment, but in the third embodiment, the temperature (not the flow-rate) of the temperature-controlling gas is modulated. The third embodiment preferably uses modulation furnaces which have a relatively low thermal mass, such that the sample/reference temperature can be modulated at relatively high modulation rates.

52 Claims, 3 Drawing Sheets

U.S. PATENT DOCUMENTS

| | | |
|---|---|---|
| 4,848,921 | 7/1989 | Kunze . |
| 4,928,254 | 5/1990 | Knudsen et al. . |
| 5,046,858 | 9/1991 | Tucker . |
| 5,098,196 | 3/1992 | O'Neill . |
| 5,152,607 | 10/1992 | Ibar . |
| 5,224,775 | 7/1993 | Reading et al. . |
| 5,248,199 | 9/1993 | Reading . |
| 5,439,291 | 8/1995 | Reading . |

OTHER PUBLICATIONS

N. Birge and S. Nagel, "Wide–frequency specific heat spectrometer," Rev. Sci. Instrum., vol. 58, Aug. 1987, pp. 1464–1470.

S. G. Black and G. S. Dixon, "AC Calorimetry of Dimyristoylphosphatidylcholine Multilayers: Hysteresis and Annealing near the Gel to Liquid–Crystal Transition," Biochemistry, vol. 20, 1991, pp. 6740–6744.

G. S. Dixon, S. G. Black, C. T. Butler and A. K. Jain, "A Differential AC Calorimeter for Biophysical Studies," Analytical Biochemistry, 121, 1982, pp. 55–61.

K. Drong, I. Lamprecht and Th. Plesser, "Calorimetric Measurements of an Intermittency Phenomenon in Oscillating Glycolysis in Cell–Free Extracts from Yeast," Thermochimica Acta, vol. 151, 1989, pp. 69–81.

V. V. Filimonov, S. A. Potekhin, S. V. Matveev and P. L. Privalov, "Thermodynamic Analysis of Scanning Microcalorimetric Data," Biophysical Chemistry, vol. 87, 1987, pp. 87–96.

E. Freire and R. L. Biltonen, "Statistical Mechanical Deconvolution of Thermal Transitions in Macromolecules. I. Theory and Application to Homogeneous Systems," Biopolymers, vol. 17, pp. 463–479 (1978).

E. Freire, W. W. van Osdol, O. L. Mayorga and J. M. Sanchez–Ruiz, "Calorimetry Determined Dynamic of Complex Unfolding Transitions in Proteins," Annu. Rev. Biophys. Biophys. Chem. 1990. 19: 159–88.

R. Garcia, "Scanning Tunneling Microscopy in Biology: Changing the Pace," Microscopy and Analysis Jul. 1991, pp. 27–29.

J. E. Graebner, "Modulated–bath calorimetry," Review of Scientific Instruments, Jun. 1989, pp. 1123–1128.

I. Hatta and A. Ikushima, "Studies on Phase Transitions by AC Calorimetry," Japanese Journal of Applied Physics, vol. 20, No. 11, Nov. 1981, pp. 1995–2011.

M. Hietschold, P. K. Hansma, A. L. Weisenhorn, "Scanning–Probe–Microscopy and Spectroscopy in Materials Science," Microscopy and Analysis, Sep. 1991, pp. 25–27.

S. Ikeda and Y. Ishikawa, "Improvement of AC Calorimetry," Japanese Journal of Applied Physics, vol. 18, No. 7, Jul. 1979, pp. 1367–1372.

S. Imaizumi, T. Matsuda and I. Hatta, "Measurement of Dynamic Specific Heat Capacity of Lysozyme Crystals," Journal of the Physical Society of Japan, vol. 47, No. 5, Nov. 1979, pp. 1643–1646.

D. H. Jung, T. W. Kwon, D. J. Bae, I. K. Moon and Y. H. Jeong, "Fully automated dynamic calorimeter," Meas. Sci. Technol., vol. 3, 1992, pp. 475–484.

S. MacPherson, "Atomic Resolution," Laboratory News, Mar. 19, 1990.

O. L. Mayorga, W. V. van Osdol, J. L. Lacomba and E. Freire, "Frequency spectrum of enthalpy fluctuations associated with macromolecular transitions," Proc. Natl. Acad. Sci. U.S.A., vol. 85, Dec. 1988, pp. 9514–9518.

O. L. Mayorga and E. Freire, "Dynamic analysis of differential scanning calorimetry data," Biophysical Chemistry, vol. 87, 1987, pp. 87–96.

M. J. Miles, "The Application of STM/AFM To Biological Molecules," Microscopy and Analysis, Jul. 1990, pp. 7–9.

J. Mitchell, "DSC: A new design for evaluating the thermal behavior of materials," International Laboratory, Feb. 28, 1991, pp. 44–48.

R. Point, J. L. Petit and P. C. Gravelle, "Reconstruction of Thermokinetics from Calorimetric Data by Means of Numerical Inverse Filters," Journal of Thermal Analysis, vol. 17, 1979, pp. 383–393.

H. S. Rade, "Wechselstromkalorimetrie–ein empfindliches und kontinuierlich registrierendes Verfahren zur Messung spezifischer Warmen kleiner Proben," Feinwerktechnik & Messtechnik, Jul. 1977, pp. 223–226.

A. Rosencwaig, "Photoacoustic microscopy," International Laboratory, Sep./Oct. 1979, pp. 37–43.

P. Sullivan and G. Seidel, "Steady–rate, ac–Temperature Calorimetry," Physical Review, vol. 173, No. 3, Sep. 15, 1968, pp. 679–685.

N. F. van Hulst and F. B. Segerink, "Optical Microscopy Beyond the Diffraction Limit," Microscopy and Analysis, Jan. 1992, pp. 21–23.

W. W. van Osdol, O. L. Mayorga and E. Freire, "Multifrequency calorimetry of the folding/unfolding transition of cytochrome c," Biophysical Journal, vol. 59, 1991, pp. 48–54.

W. W. Wendlandt, "Thermal Methods of Analysis," Dept. of Chemistry, University of Houston, Houston, Texas, Second Edition, 1974, pp. 193–212.

C. C. Williams and H. K. Wickramasinghe, "Photothermal Imaging with Sub–100–nm Spatial Resolution," Photoacoustic and Photothermal Phenomena Proceedings, pp. 364–368.

H. Yao and I. Hatta, "An ac Microcalorimetric Method for Precise Heat Capacity Measurement in a Small Amount of Liquid," Japanese Journal of Applied Physics, Jan. 1988. pp. 121–122.

Ulvac Sinku–Riko, Inc. product brochure ACC–1, "AC Calorimeter," publication date unknown, Catalog No. 8909–A13E/90.71000.

Ulvac Sinku–Riko, Inc. product brochure, "Thermal Constants Analyzer by AC Calorimetric Method," publication date unknown, Catalog No. 9010–P1TR1/90.10.3000.

Ulvac Sinku–Riko, Inc. product brochure ACC–VL1, "AC Calorimeter," publication date unknown, Catalog No. 9102–A24E.

Microscopy and Analysis, "Aris Scanning Tunneling Microscope," Jan. 1992.

Di product brochure, "Nanoscope II, Scanning Tunneling Microscope," publication date unknown.

Struers product brochure, "Welcome to the World of Atoms, Tunnelscope 2400," publication date unknown.

Struers product brochure, "Welcome to the World of Atoms, Tunnelscope 2400, Software Version 2.0," publication date unknown.

Maesono, A. and Kato, R., "Recently Developed Instruments Relevant to AC Calorimetry," Netsu Sokutei no Shimpo, vol. 5, pp. 71–78 (1987), (with translation).

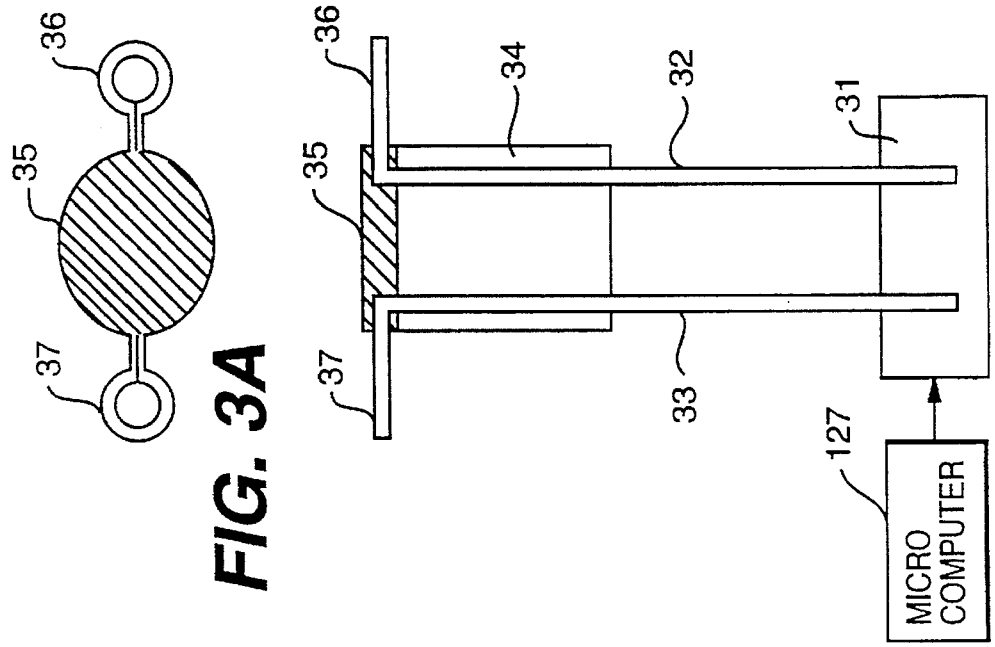
FIG. 3A
FIG. 3B
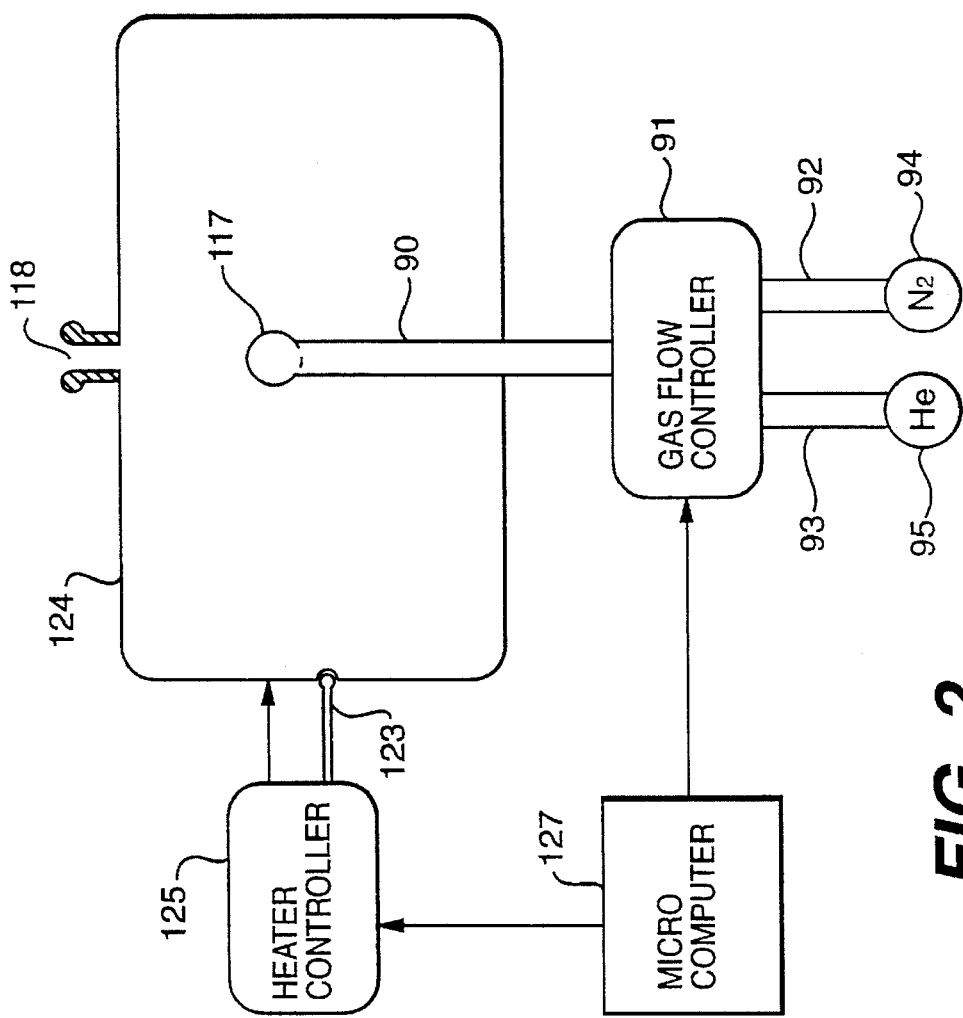
FIG. 2

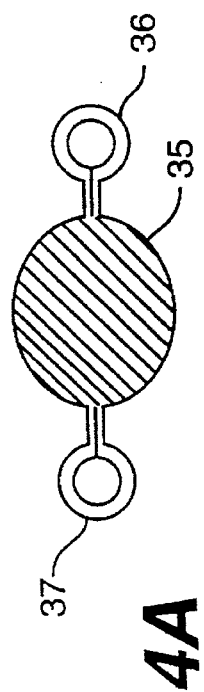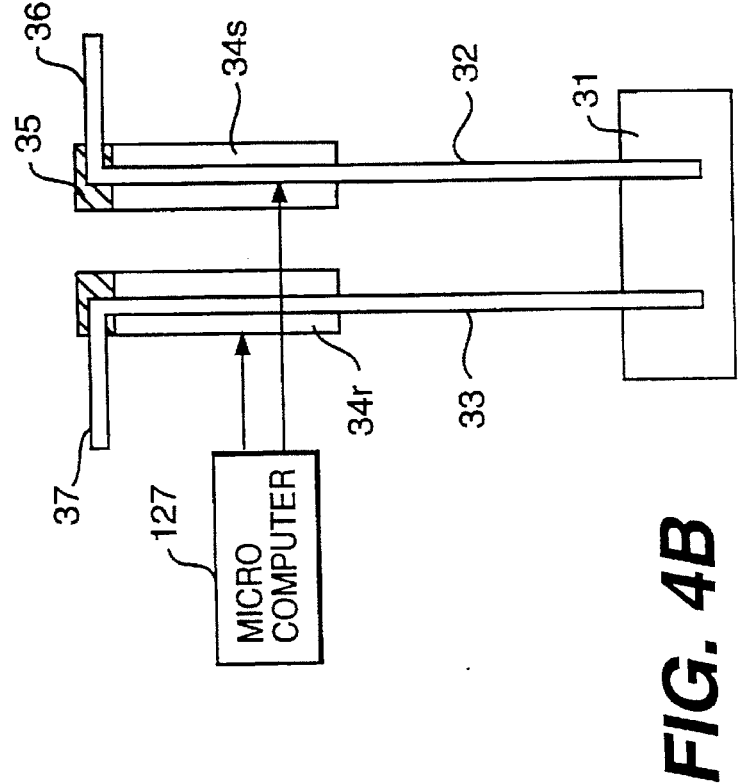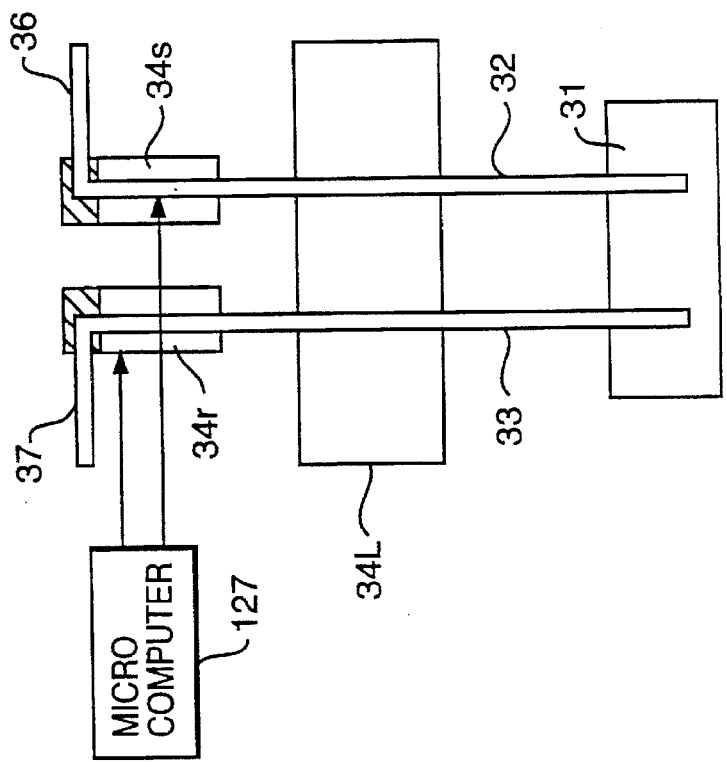
FIG. 4A
FIG. 4B
FIG. 5

METHOD AND APPARATUS FOR GAS FLOW MODULATED DIFFERENTIAL SCANNING CALORIMETRY

This application is a continuation-in-part of application Ser. No. 171,656, filed on Dec. 22, 1993, now issued as U.S. Pat. No. 5,439,291, which is a continuation-in-part of application Ser. No. 060,214, filed on May 7, 1993, now issued as U.S. Pat. No. 5,346,306, which is a continuation of application Ser. No. 844,448, filed Mar. 2, 1992, now issued as U.S. Pat. No. 5,224,775.

BACKGROUND

1. Field of the Invention

The present invention relates to methods and apparatus for modulating the temperature of a modulated differential scanning calorimeter ("MDSC") by modulating characteristics of gas in thermal contact with the sample and/or the reference in the MDSC.

2. Background of the Invention

Modulated differential scanning calorimetry and differential thermal analysis are described in the above-referenced patents and patent applications, which are hereby incorporated by reference. Briefly, differential scanning calorimetry ("DSC") is an analytical technique in which the heat flow associated with a chemical, physical or crystallographic transformation in a material is measured as a function of temperature and time (and possibly pressure). Modulated differential scanning calorimetry is an advanced technique, in which the total heat flow signal is obtained as the temperature of the sample and/or reference is heated according to a basic heating rate upon which a temperature oscillation has been superimposed. The total heat flow signal can then be deconvoluted to obtain one or more deconvoluted signals representative of, e.g., the rapidly-reversible and/or nonrapidly-reversible components of the heat flow.

Major advantages of MDSC include (1) the ability to separately measure one or more components of the total heat flow signal; (2) an improved ability, compared to conventional DSC, to measure transformations or other thermal events which are overlapped in temperature and/or in time; and (3) improved resolution by allowing for the use of a relatively slow underlying heating rate.

DEFINITIONS

"Transition" or "Transformation", as used herein, mean any type of physical or chemical transformation, phase change, or structural change in a material.

"Analyzing", as used herein with respect to a material, means determining the composition, phase, structure, and/or identity of the material.

"Rapidly reversible", as used herein, means any portion of a signal, transition, or event which is a direct function of the rate of change of temperature. For example, the contribution to the heat flow signal in DSC attributable to the rate of change of temperature of the sample material is a rapidly reversible transition. In DSC, for example, one of the contributions to the rapidly reversible portion of the heat flow signal is the heat capacity of the sample material. Rapidly reversible processes include those processes which are thermodynamically reversible and have small kinetic time constants relative to the rate of change of the driving variable.

"Non-rapidly reversible", as used herein, means any portion of a signal, transition or event which is a direct function of the value of temperature. For example, the contribution to the heat flow signal in DSC attributable to the absolute temperature of the sample material is a non-rapidly reversible transition. This might be caused by a chemical or physical change taking place such as recrystallization. Non-rapidly reversible processes include those processes which are thermodynamically irreversible, as well as processes which are thermodynamically reversible, but which reverse very slowly relative to the rate of change of the driving variable due to the kinetic limitations of the process.

"Deconvolution", as used herein, means the process of separating the dependence of heat flow into one or more component parts so that each component part can be utilized or analyzed separately. For example, the dependence of the heat flow can be deconvoluted into a rapidly reversible component and/or a non-rapidly reversible component.

"Signal baseline", as used herein, means that portion of a signal representing the value of heat flow obtained in a range in which there are no transitions or transformations.

"Sensitivity" of an analytical technique, as used herein, means the degree to which signals associated with transitions can be physically distinguished from the signal baseline in the analytical data produced by the technique. This quality of the analytical technique is most critical when the temperature is changing very slowly.

"Resolution" of an analytical technique, as used herein, means the degree to which signals associated with different transitions can be physically separated in the analytical data produced by the technique. This quality of the analytical technique is most critical when multiple transitions occur at closely spaced values of temperature.

"Sample/Reference", as used herein, shall mean the sample material or the reference material, or both.

A gas shall be in "thermal contact" with the sample/reference, if heat can be effectively transferred from the gas to the sample/reference.

SUMMARY OF THE INVENTION

The present invention modulates a differential scanning calorimeter ("DSC") by modulating the characteristics of a gas in thermal contact with the sample and/or the reference in the DSC. The present invention allows the use of MDSC at high modulation rates, compared to the modulation rates used with MDSC as described in U.S. Pat. No. 5,224,775.

In the first embodiment of the present invention, the major heat flow path between the sample/reference and the furnace is the purge gas in the furnace chamber. The composition of the purge gas in the furnace chamber of a DSC cell is modulated by alternately purging the DSC with a high thermal conductivity gas (e.g., helium) and with a low thermal conductivity gas (e.g., nitrogen). This modulates the characteristics of the DSC cell.

When there is no heat flow between the sampled reference and the furnace, because the sample and reference are in equilibrium with the furnace, the composition of the purge gas is irrelevant, and there is no modulated signal.

However, if the sample is not in thermal equilibrium with its surroundings, modulating the thermal conductivity of the purge gas modulates the flow of heat to the sample/reference, and thus produces a modulated signal. Because typical DSC cells have relatively small volumes, MDSCs can be modulated at relatively high rates using this technique.

If the temperature of the furnace is modulated at one frequency, and the composition of the purge gas is modulated at substantially different frequency (e.g., a frequency differing by a factor of five from the frequency of the temperature modulation), then a multiplexed signal would be produced.

In the second embodiment of the present invention, the sample and reference are heated (or cooled) by a temperature-controlling gas flowing around the sample and reference holders. The gas is heated by being passed through a furnace before it flows around the sample and the reference. The flow-rate of the temperature-controlling gas is modulated, thus modulating the temperature of the sample and the reference.

The third embodiment is similar to the second embodiment, but in the third embodiment, the temperature of the temperature-controlling gas is modulated (instead of its flow rate). In this embodiment, a combination of furnaces may be used to obtain the desired sample and reference temperatures. For example, a relatively large thermal mass furnace may be used for the linear (or heating ramp) portion of the sample and reference temperatures, and separate low thermal mass furnaces may be used to modulate the sample/reference temperatures. Because the thermal mass of the modulation furnaces is relatively low, the sample/reference temperatures can be modulated at relatively high modulation rates.

Accordingly, it is an object of the present invention to provide improved methods and apparatus for modulating the temperature of a sample and/or a reference in a modulated differential scanning calorimeter.

It is another object of the present invention to modulate the heat flow to and from a sample and a reference in an MDSC by modulating the composition of the purge gas in the MDSC.

It is another object of the present invention to modulate the temperature of a sample and/or a reference in an MDSC by modulating the flow rate of a gas controlling the temperature of the sample and/or a reference in the MDSC.

It is another object of the present invention to modulate the temperature of a sample and/or a reference in an MDSC by modulating the temperature of a gas controlling the temperature of the sample and/or a reference in the MDSC.

BRIEF DESCRIPTION OF THE DRAWINGS

FIG. 2 is a schematic diagram of a modulated differential scanning calorimeter configured according to the first embodiment of the present invention.

FIGS. 3A and 3B is a schematic diagram of a modulated differential scanning calorimeter configured according to the second embodiment of the present invention.

FIGS. 4A and 4B is a schematic diagram of a modulated differential scanning calorimeter configured according to the third embodiment of the present invention, which uses independent modulation furnaces for the sample and the reference.

FIG. 5 is a schematic diagram of a modulated differential scanning calorimeter configured according to the third embodiment of the present invention, which uses one heat ramp furnace and two modulation furnaces.

DETAILED DESCRIPTION OF THE INVENTION

Figure 1:
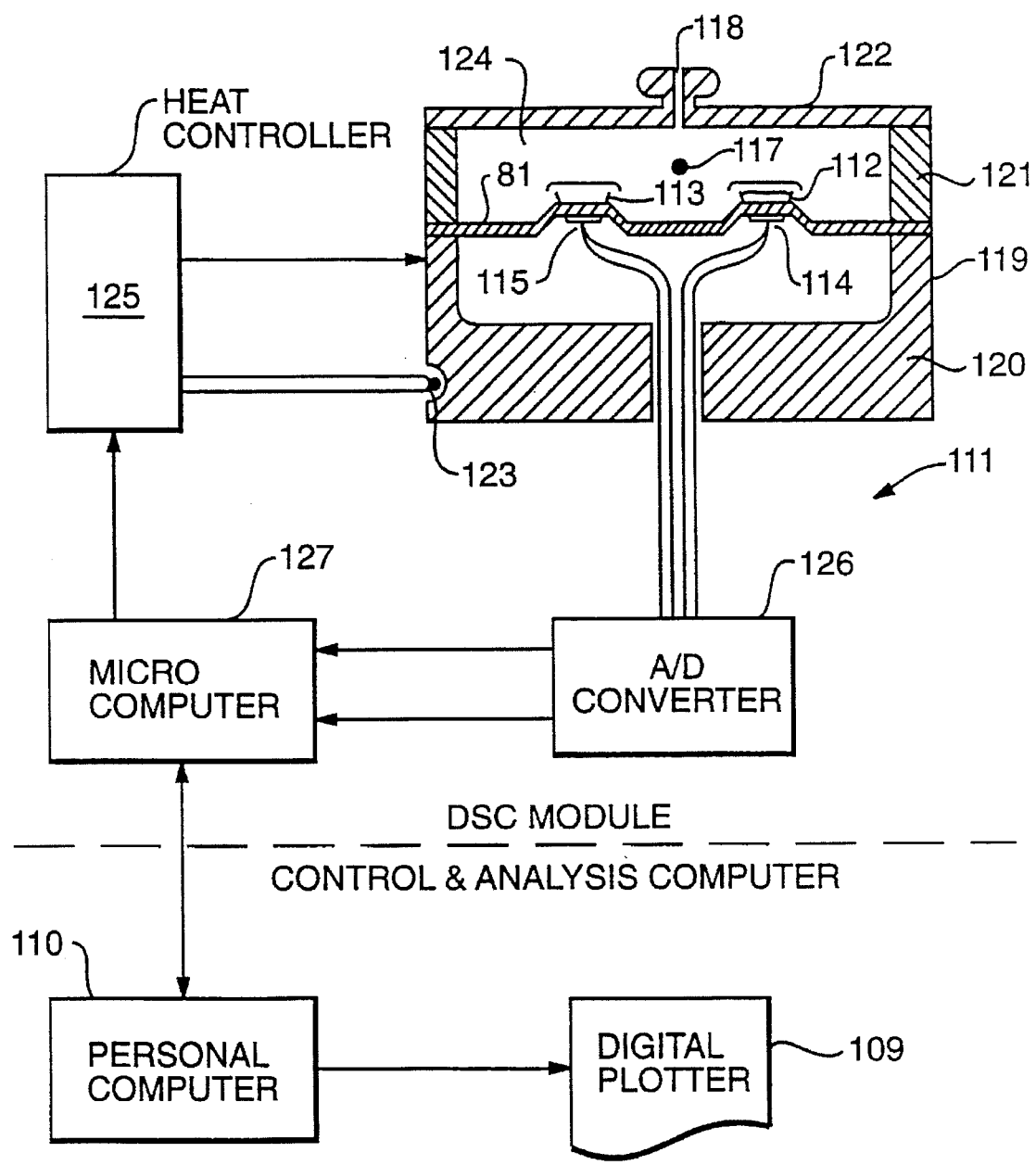
FIG. 1 is a schematic diagram of a modulated differential scanning calorimeter.

FIGS. 1 and 2 are schematic diagrams of the first embodiment of the present invention. FIG. 1 includes a side view of the interior of the furnace chamber. FIG. 1 is similar to FIG. 1 of U.S. Pat. No. 5,224,775 (the "'775 patent"), and is explained in detail therein. However, FIG. 1 differs in one significant respect from FIG. 1 of the '775 patent. Thermoelectric 116 element in the '775 patent serves as the major heat flow path for transferring heat from the furnace to sample and the reference. In the first embodiment, the purge gas in the furnace chamber constitutes a major heat flow path for transferring heat to the sample and the reference. Element 81 in FIG. 1 may be a thermoelectric element similar to element 116 of the '775 patent (in which case it would be a second major heat flow path, operating in parallel with the purge gas). Element 81 may also be an insulator, in which case it functions mainly as a support for the sample and the reference, i.e., it only plays a minor role (or essentially no role) in the transfer of heat to/from the sample/reference.

FIG. 1 shows purge gas inlet 117, which is positioned slightly above the midpoint between sample pan 112 and reference pan 113. FIG. 1 also shows purge gas outlet 118.

FIG. 2 is a side view of the exterior of furnace chamber 124. It shows how the apparatus of the '775 patent can be modified to implement the first embodiment of the present invention. FIG. 2 shows furnace chamber 124 with purge gas inlet 117 and purge gas outlet 118. Tube 90 provides a fluid path from gas flow controller 91 to purge gas inlet 117. Gas flow controller 91 supplies either a high thermal conductivity gas, e.g., He, from gas supply 95 or a low thermal conductivity gas, e.g., $N_2$, from gas supply 94. In the example shown in FIG. 2, gas flow controller 91 is controlled by microcomputer 127. Gas flow controller 91 could alternatively be controlled by personal computer 110 (shown in FIG. 1).

In the apparatus shown in FIGS. 1 and 2, two gases, one gas having a relatively high thermal conductivity, e.g., helium, and a second gas having a relatively low thermal conductivity, e.g., nitrogen, are used to alternately purge the sample and/or the reference. If the temperature of the sample and/or the reference is the same as the temperature of the surrounding apparatus, there will be no MDSC signal produced (because the thermal conductivity of the gas will have no effect on the heat flow to/from the sample and the reference). However, if the temperature of the sample and/or the reference differs significantly from the temperature of the surrounding apparatus, an MDSC signal will be produced. Thus, in this embodiment, a characteristic of the calorimeter is modulated, which results in a modulation of the heat flow to/from the sample and/or the reference.

FIGS. 3A and 3B are a schematic diagram of the second embodiment of the present invention. FIGS. 3A and 3B show a sample 36 and a reference 37 in a differential calorimeter cell in a DSC. A furnace 34 is used to control the temperature and heating rate of the DSC. Heat from furnace 34 is carried to the sample and the reference via a heating gas, e.g., helium gas, flowing through tubes 32 and 33. The temperature of the sample 36 and/or the reference 37 can then be modulated by modulating the flow of gas to the sample and/or the reference, using flow controller 31. The sample and the reference are thermally isolated by an insulating platform 35. The differential flow of heat to/from the sample with respect to the reference is then measured using conventional techniques, as described in the '775 patent.

After it has passed through the sample and reference holders, the heating gas may be purged into the furnace chamber, vented outside the furnace chamber, or brought back in through flow controller 31. In the latter case, the gas is flowing continuously in one direction around a closed loop. Flow controller 31 receives the gas after it has passed around sample 36 or reference 37, and then releases it into tubes 32 and 33 under the control of microcomputer 127.

Alternatively, flow controller 31 may modulate the temperature of sample 36 and/or reference 37 by controlling the flow of the gas around sample 36 and reference 37 in a reciprocal fashion. In that case, the gas is not vented to the atmosphere or released into the purge chamber, but is pumped back and forth from the sample and/or reference to furnace 34. The reciprocal flow of gas around the sample and the reference induces a modulation of the temperature of the sample and reference.

The third embodiment of the present invention is similar to the second embodiment, except that the flow rate of the gas is held constant, and the temperature of the gas is modulated. FIGS. 4A and 4B are similar to FIGS. 3A and 3B, respectively, except that heater 34 has been replaced by heaters 34s and 34r, and microcomputer 127 controls the temperature of furnaces 34s and 34r instead of controlling flow controller 31. The furnace used in this embodiment can have a relatively small thermal mass (i.e., a thermal mass substantially smaller than the thermal mass of the furnace used in conventional MDSC), thus allowing for much higher modulation frequencies than in conventional MDSC instruments.

Alternatively, this embodiment can be implemented using one furnace having a relatively large thermal mass, and one or two additional low thermal mass furnaces. The large thermal mass furnace (the "heat ramp furnace") would be used to provide the linear or heat ramp component of the temperature to the sample and the reference. Low thermal mass furnaces (the "modulation furnaces") would be used to provide the temperature modulation components. A single modulation furnace could be used to simultaneously modulate the temperature of the sample and the reference, or to modulate only the temperature of the sample, or to modulate only the temperature of the reference. Two modulation furnaces could be used to independently modulate the temperature of the sample and the temperature of the reference.

In the example of the third embodiment shown in FIGS. 4A and 4B, the temperature of the sample and/or the reference can be independently controlled using furnaces 34s and 34r. As discussed in the preceding paragraph, the third embodiment could also be implemented using a single furnace to modulate the sample and the reference simultaneously (such as furnace 34 shown in FIG. 3B), or using only one of furnaces 34s and 34r to modulate either the sample or the reference. FIG. 5 shows an implementation of the third embodiment which uses a large thermal mass furnace 34L to provide the linear or heat ramp component of the sample and reference temperatures, in addition to small thermal mass modulation furnaces 34s (which modulates the sample temperature) and 34r (which modulates the reference temperature).

The waveform of the temperature modulation can be any periodic function, including the sinusoidal, square, triangular, sawtooth and pulse functions, or combinations of any of these functions. The temperature of the sample/reference would then be subjected to the periodic modulation function combined with a linear temperature ramp. For example, the combined function could be a step function which is the combination of a linear function with a sawtooth function. Moreover, although the present invention has been described in terms of heating the sample/reference, it could equally be used in MDSC instruments in which the sample/reference are cooled according to a combination of a temperature modulation superimposed upon a linear cooling ramp.

The foregoing disclosure of embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. A gas flow modulated differential scanning calorimeter comprising:
   (a) means for varying the temperature of a sample/reference in a cell in the differential scanning calorimeter according to an underlying heating rate;
   (b) means for selecting a modulation frequency and a modulation amplitude;
   (c) means for controlling the temperature of the sample/reference according to the selected underlying heating rate, modulation frequency and modulation amplitude;
   (d) means for detecting the heat flow to and from the sample/reference with respect to a reference as a function of temperature, as the temperature of the sample/reference is varied according to the modulation frequency and modulation amplitude;
   (e) means for recording a signal representative of differential changes in the heat flow to and from the sample/reference; and
   (f) means for deconvoluting the signal representative of differential changes in the heat flow to compute at least one deconvoluted signal, wherein the temperature of the sample/reference is modulated by controlling the characteristics of a flow of gas in thermal contact with the sample/reference.

2. The gas flow modulated differential scanning calorimeter of claim 1, wherein the temperature of the sample/reference is modulated by controlling the composition of the flow of gas in thermal contact with the sample/reference.

3. The gas flow modulated differential scanning calorimeter of claim 2, wherein the flow of gas in thermal contact with the sample/reference is a purge gas.

4. The gas flow modulated differential scanning calorimeter of claim 3, wherein the temperature of the sample/reference is modulated by alternately switching the purge gas from a high thermal conductivity purge gas to a low thermal conductivity purge gas.

5. The gas flow modulated differential scanning calorimeter of claim 4, wherein the high thermal conductivity gas is helium.

6. The gas flow modulated differential scanning calorimeter of claim 4, wherein the low thermal conductivity gas is nitrogen.

7. The gas flow modulated differential scanning calorimeter of claim 1, wherein the means for varying the temperature of the sample/reference comprises a means for modulating the flow rate of the gas in thermal contact with the sample/reference.

8. The gas flow modulated differential scanning calorimeter of claim 7, wherein the gas in thermal contact with the sample/reference is helium.

9. The gas flow modulated differential scanning calorimeter of claim 7, wherein the gas in thermal contact with the sample/reference is contained within tubing that is muted around the sample/reference.

10. The gas flow modulated differential scanning calorimeter of claim 9, wherein the gas in thermal contact with the sample/reference is released into the cell.

11. The gas flow modulated differential scanning calorimeter of claim 9, wherein the gas in thermal contact with the sample/reference flows continuously and unidirectionally around a closed loop from the means for modulating the flow rate, to the sample/reference, and on to the means for modulating the flow rate.

12. The gas flow modulated differential scanning calorimeter of claim 9, wherein the gas in thermal contact with the sample/reference flows reciprocally and bidirectionally from the means for controlling the flow rate to the sample/reference and back to the means for modulating the flow rate.

13. The gas flow modulated differential scanning calorimeter of claim 9, wherein the gas in thermal contact with the sample/reference is heated by a furnace prior to being in thermal contact with the sample/reference.

14. The gas flow modulated differential scanning calorimeter of claim 13, wherein the furnace has a relatively low thermal mass.

15. The modulated differential scanning calorimeter of claim 1, wherein the gas in thermal contact with the sample/reference is heated by a furnace prior to being in thermal contact with the sample/reference.

16. The modulated differential scanning calorimeter of claim 15, wherein the temperature of the sample/reference is modulated by modulating the temperature of the furnace.

17. The modulated differential scanning calorimeter of claim 15, wherein the furnace is a low thermal mass furnace.

18. The modulated differential scanning calorimeter of claim 15, wherein the gas in thermal contact with the sample/reference is released into the cell.

19. The gas flow modulated differential scanning calorimeter of claim 15, wherein the gas in thermal contact with the sample/reference flows continuously and unidirectionally around a closed loop from the furnace, to the sample/reference, and on to the furnace.

20. The gas flow modulated differential scanning calorimeter of claim 15, wherein the gas in thermal contact with the sample/reference flows reciprocally and bidirectionally from the furnace to the sample/reference and back to the furnace.

21. The gas flow modulated differential scanning calorimeter of claim 1, wherein the means for deconvoluting the signal representative of differential changes in the heat flow comprises means for deconvoluting a rapidly-reversible component of the differential changes in the heat flow.

22. The gas flow modulated differential scanning calorimeter of claim 1, wherein the means for deconvoluting the signal representative of differential changes in the heat flow comprises means for deconvoluting a nonrapidly-reversible component of the differential changes in the heat flow.

23. The gas flow modulated differential scanning calorimeter of claim 1, wherein the means for deconvoluting the signal representative of differential changes in the heat flow comprises means selected from one of means for deconvoluting a rapidly-reversible component of the differential changes in the heat flow and means for deconvoluting a nonrapidly-reversible component of the differential changes in the heat flow.

24. The gas flow modulated differential scanning calorimeter of claim 23, wherein the temperature of the sample/reference is modulated by controlling the composition of the flow of gas in thermal contact with the sample/reference.

25. The gas flow modulated differential scanning calorimeter of claim 24, wherein the flow of gas in thermal contact with the sample/reference is a purge gas.

26. The gas flow modulated differential scanning calorimeter of claim 25, wherein the temperature of the sample/reference is modulated by alternately switching the purge gas from a high thermal conductivity purge gas to a low thermal conductivity purge gas.

27. The gas flow modulated differential scanning calorimeter of claim 23, wherein the means for varying the temperature of the sample/reference comprises a means for modulating the flow rate of the gas in thermal contact with the sample/reference.

28. The gas flow modulated differential scanning calorimeter of claim 27, wherein the gas in thermal contact with the sample/reference is helium.

29. The gas flow modulated differential scanning calorimeter of claim 27, wherein the gas in thermal contact with the sample/reference is contained within tubing that is routed around the sample/reference.

30. The gas flow modulated differential scanning calorimeter of claim 29, wherein the gas in thermal contact with the sample/reference is released into the cell.

31. The gas flow modulated differential scanning calorimeter of claim 29, wherein the gas in thermal contact with the sample/reference flows continuously and unidirectionally around a closed loop from the means for modulating the flow rate, to the sample/reference, and on to the means for modulating the flow rate.

32. The gas flow modulated differential scanning calorimeter of claim 29, wherein the gas in thermal contact with the sample/reference flows reciprocally and bidirectionally from the means for controlling the flow rate to the sample/reference and back to the means for modulating the flow rate.

33. The gas flow modulated differential scanning calorimeter of claim 29, wherein the gas in thermal contact with the sample/reference is heated by a furnace prior to being in thermal contact with the sample/reference.

34. The gas flow modulated differential scanning calorimeter of claim 33, wherein the furnace has a relatively low thermal mass.

35. The modulated differential scanning calorimeter of claim 23, wherein the gas in thermal contact with the sample/reference is heated by a furnace prior to being in thermal contact with the sample/reference.

36. The modulated differential scanning calorimeter of claim 35, wherein the temperature of the sample/reference is modulated by modulating the temperature of the furnace.

37. The modulated differential scanning calorimeter of claim 35, wherein the furnace is a low thermal mass furnace.

38. The modulated differential scanning calorimeter of claim 35, wherein the gas in thermal contact with the sample/reference is released into the cell.

39. The gas flow modulated differential scanning calorimeter of claim 35, wherein the gas in thermal contact with the sample/reference flows continuously and unidirectionally around a closed loop from the furnace, to the sample/reference, and on to the furnace.

40. The gas flow modulated differential scanning calorimeter of claim 35, wherein the gas in thermal contact with the sample/reference flows reciprocally and bidirectionally from the furnace to the sample/reference and back to the furnace.

41. A gas flow modulated differential scanning calorimeter comprising:
    (a) means for varying the temperature of a sample/reference in a cell in the differential scanning calorimeter according to an underlying heating rate;
    (b) means for selecting a modulation frequency and a modulation amplitude;

(c) means for controlling the temperature of the sample/reference according to the selected underlying heating rate, modulation frequency and modulation amplitude;

(d) means for detecting the heat flow to and from the sample/reference with respect to a reference as a function of temperature, as the temperature of the sample/reference is varied according to the modulation frequency and modulation amplitude;

(e) means for recording a signal representative of differential changes in the heat flow to and from the sample/reference; and (f) means for deconvoluting the signal representative of differential changes in the heat flow to compute at least one deconvoluted signal, wherein the gas in thermal contact with the sample/reference is a heating gas, and the temperature of the sample/reference is modulated by modulating the flow rate of the heating gas as it flows through a furnace prior to being in thermal contact with the sample/reference.

42. The gas flow modulated differential scanning calorimeter of claim 41, wherein the gas in thermal contact with the sample/reference is helium.

43. The gas flow modulated differential scanning calorimeter of claim 41, wherein the gas in thermal contact with the sample/reference is released into the cell.

44. The gas flow modulated differential scanning calorimeter of claim 41, wherein the gas in thermal contact with the sample/reference flows continuously and unidirectionally around a closed loop from the means for modulating the flow rate, through the furnace, to the sample/reference, and on to the means for modulating the flow rate.

45. The gas flow modulated differential scanning calorimeter of claim 41, wherein the gas in thermal contact with the sample/reference flows reciprocally and bidirectionally from the means for controlling the flow rate to the sample/reference and back to the means for modulating the flow rate.

46. The gas flow modulated differential scanning calorimeter of claim 41, wherein the furnace has a relatively low thermal mass.

47. A gas flow modulated differential scanning calorimeter comprising:

(a) means for varying the temperature of a sample/reference in a call in the differential scanning calorimeter according to an underlying heating rate;

(b) means for selecting a modulation frequency and a modulation amplitude;

(c) means for controlling the temperature of the sample/reference according to the selected underlying heating rate, modulation frequency and modulation amplitude;

(d) means for detecting the heat flow to and from the sample/reference with respect to a reference as a function of temperature, as the temperature of the sample/reference is varied according to the modulation frequency and modulation amplitude;

(e) means for recording a signal representative of differential changes in the heat flow to and from the sample/reference; and (f) means for deconvoluting the signal representative of differential changes in the heat flow to compute at least one deconvoluted signal, wherein the gas in thermal contact with the sample/reference is a heating gas that is heated by a furnace prior to coming into thermal contact with the sample/reference, and the temperature of the sample/reference is modulated by modulating the temperature of the furnace.

48. The gas flow modulated differential scanning calorimeter of claim 47, wherein the gas in thermal contact with the sample/reference is helium.

49. The gas flow modulated differential scanning calorimeter of claim 47, wherein the gas in thermal contact with the sample/reference is released into the cell.

50. The gas flow modulated differential scanning calorimeter of claim 47, wherein the gas in thermal contact with the sample/reference flows continuously and unidirectionally around a closed loop through the furnace, to the sample/reference, and on to the furnace again.

51. The gas flow modulated differential scanning calorimeter of claim 47, wherein the gas in thermal contact with the sample/reference flows reciprocally and bidirectionally from the furnace to the sample/reference and back again.

52. The gas flow modulated differential scanning calorimeter of claim 47, wherein the furnace has a relatively low thermal mass.

* * * * *